US010456353B2

(12) United States Patent
Kalathil et al.

(10) Patent No.: US 10,456,353 B2
(45) Date of Patent: Oct. 29, 2019

(54) PERSONAL CARE COMPOSITIONS

(71) Applicant: Conopco, Inc., Englewood Cliffs, NJ (US)

(72) Inventors: Ramitha Kalathil, Bangalore (IN); Amitabha Majumdar, Bangalore (IN); Suman Majumder, Mumbai (IN); Jagannath Taduri, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 175 days.

(21) Appl. No.: 15/304,130

(22) PCT Filed: Apr. 1, 2015

(86) PCT No.: PCT/EP2015/057145
§ 371 (c)(1),
(2) Date: Oct. 14, 2016

(87) PCT Pub. No.: WO2015/158550
PCT Pub. Date: Oct. 22, 2015

(65) Prior Publication Data
US 2017/0035686 A1 Feb. 9, 2017

(30) Foreign Application Priority Data
Apr. 17, 2014 (EP) .................. 14165157

(51) Int. Cl.
*A61K 8/97* (2017.01)
*A61K 8/73* (2006.01)
*A61Q 19/00* (2006.01)
*A61K 31/728* (2006.01)
*A61K 36/886* (2006.01)
*A61Q 5/00* (2006.01)
*A61Q 11/00* (2006.01)

(52) U.S. Cl.
CPC .............. *A61K 8/97* (2013.01); *A61K 8/735* (2013.01); *A61K 31/728* (2013.01); *A61K 36/886* (2013.01); *A61Q 5/002* (2013.01); *A61Q 11/00* (2013.01); *A61Q 19/00* (2013.01); *A61Q 19/007* (2013.01); *A61K 2800/59* (2013.01); *A61Q 5/006* (2013.01)

(58) Field of Classification Search
CPC .............. A61K 2800/59; A61K 31/715; A61K 31/728; A61K 36/886; A61K 8/735; A61K 8/97; A61K 2800/80; A61Q 11/00; A61Q 19/00; A61Q 19/007; A61Q 5/002; A61Q 5/006
See application file for complete search history.

(56) References Cited

U.S. PATENT DOCUMENTS

| 4,735,935 | A | 4/1988 | McAnalley |
| 5,723,673 | A | 3/1998 | Kao et al. |
| 5,824,659 | A | 10/1998 | Strickland et al. |
| 5,888,984 | A | 3/1999 | Brown |
| 5,902,796 | A | 5/1999 | Shand et al. |
| 6,436,679 | B1 | 8/2002 | Qiu et al. |
| 6,482,942 | B1 | 11/2002 | Vittori |
| 2002/0009438 | A1 | 1/2002 | Shupe et al. |
| 2003/0096378 | A1 | 5/2003 | Qiu et al. |
| 2004/0038931 | A1 | 2/2004 | Elsobly et al. |
| 2005/0019433 | A1 | 1/2005 | Van Dijk et al. |
| 2010/0255130 | A1 | 10/2010 | DeBaun et al. |
| 2011/0172181 | A1 | 7/2011 | Danhof |
| 2013/0129844 | A1* | 5/2013 | Claret .............. A61K 8/735 424/729 |

FOREIGN PATENT DOCUMENTS

| CN | 1418892 | | 5/2003 |
| CN | 1418892 A | * | 5/2003 |
| CN | 1424330 | | 6/2003 |
| CN | 1948346 | | 4/2007 |
| CN | 101693002 | | 4/2010 |
| CN | 102101893 | | 6/2011 |
| CN | 103622864 | | 3/2014 |
| ES | 2224881 | | 7/2006 |
| FR | 2932386 | | 12/2009 |
| FR | 2924023 | | 12/2010 |
| JP | 59013709 | | 1/1984 |
| JP | 62263193 | | 11/1987 |
| JP | 2000143527 | | 5/2000 |
| KR | 19960037059 | | 11/1996 |
| KR | 20120101897 | | 9/2012 |
| WO | WO2006056801 | | 6/2006 |
| WO | WO2012094010 | | 7/2012 |

OTHER PUBLICATIONS

Amicon "Amicon Ultra 0.5 mL centrifugal filters: MWCO 3 kDA" Sigma-Aldrich (Millipore Sigma), Jun. 15, 2009, <URL: www.sigmaaldrich.com/catalog/product/aldrich/z677094?lang=en&region=US>, retrieved Apr. 1, 2018, 4 pages. (Year: 2009).*
Search Report and Written Opinion in EP14165157, dated Oct. 28, 2014.
Search Report for PCTEP2015057145, dated Jul. 28, 2015, WO.
Search Report in PCTEP2015057292, dated Sep. 15, 2015.
Written Opinion in PCTEP2015057145, dated Jul. 28, 2015, WO.
Written Opinion in PCTEP2015057292, dated Sep. 15, 2015.
Co-pending Application No.; filed Oct. 10, 2016.
Ouyang et al.; Food Research and Development; pp. 153-156; no translation; vol. 29 No. 11.
Ouyang et al.; Food Research and Development; 2008, 29(11) , pp. 153-156 (English Abstract).

* cited by examiner

*Primary Examiner* — Aaron J Kosar
(74) *Attorney, Agent, or Firm* — Foley & Lardner LLP

(57) ABSTRACT

The invention relates to a personal care composition which provides enhanced inter-cellular tight junction in skin cells. The invention more particularly relates to use of such composition for application on skin, scalp, hair and oral cavity. The personal care composition comprises an extract of Aloe vera and a hyaluronic acid polymer having a molecular weight from 5 to 60 kDa.

17 Claims, No Drawings

PERSONAL CARE COMPOSITIONS

FIELD OF THE INVENTION

The invention relates to a personal care composition which provides enhanced inter-cellular tight junction in skin cells. The invention more particularly relates to use of such composition for application on skin, scalp, hair and oral cavity.

BACKGROUND OF THE INVENTION

People try to take good care of the external surface of their bodies as well as those of their pets to enable good overall health. Specific skin related issues that people care about include, good skin health free of infections, good skin tone and adequate moisturisation. Oral cavity is another external surface that people take active care to maintain. They prefer their oral cavity including the gums and teeth to be free of problems like cavities, tartar, gingivitis, caries, and bad breath, also known as halitosis, and plaque. Hair and scalp care are also of concern to people. People generally prefer to have thick long hair with minimum hair fall. Dandruff is a commonly occurring scalp problem for which a fungal microorganism has been implicated.

All of the above surfaces including skin, oral cavity and scalp hygiene are generally achieved by keeping them free of infections. One way to tackle infections is to treat them with antimicrobials after the infection has set in. Another approach is to leave a mimimal amount of antimicrobial active on the surface so that any invading microorganism is killed or inactivated so as to minimize spread of disease. Yet another approach has been investigated by the present inventors which is the approach of improving the innate immunity of the desired surface.

The present inventors have found that a specific combination of an Aloe vera extract together with a hyaluronic acid polymer interact synergistically to enhance inter-cellular tight junction in skin cells thereby providing enhanced moisturisation of skin and reducing chances of skin infections. The invention also relates to using such a fraction in oral care compositions for improved gum health and in hair care compositions for improving strength of hair fiber and also as a anti-dandruff agent. CN 103622864 (GUANG-DONG YALIJIE FINE CHEMICAL CO, 2014) discloses a multi-function aloe gel and preparation method thereof, the multi-function aloe gel comprising effective active ingredients such as lyophilized aloe powders, purslane extract, macromolecular sodium hyaluronate, oligomeric sodium hyaluronate, allantoin, D-panthenol, menthol, betaine, and beta-glucan, as well as methylisothiazolinone and iodo propynyl-group formic acid butyl ester as preservatives, and further comprising carbomer, and one of potassium hydroxide and sodium hydroxide solutions having a concentration of 5 percent as alkaline liquid.

US2013129844 discloses a sterile and/or decontaminated composition for topical use, including hyaluronic acid at a concentration of greater than or equal to 0.1 wt percent relative to the total weight of the composition, at least one skin wound healing agent, optionally at least one plant extract, and at least one solvent. The invention also relates to a unit including such a composition, to a method for preparing such a composition, and to the uses thereof. This publication does not specifically disclose the combination claimed in the present invention and so is not capable of exhibiting the efficacy of the composition of the present invention.

It is thus an object of the present invention to prepare an active that provides enhanced immunity to a topical surface of a human or animal body.

SUMMARY OF THE INVENTION

The present invention relates to a personal care composition comprising
(i) an extract of Aloe vera; and
(ii) a hyaluronic acid polymer having a molecular weight from 5 to 60 kDa, the hyaluronic acid having the monomeric structure;

FIG. 1. Chemical structure of HA

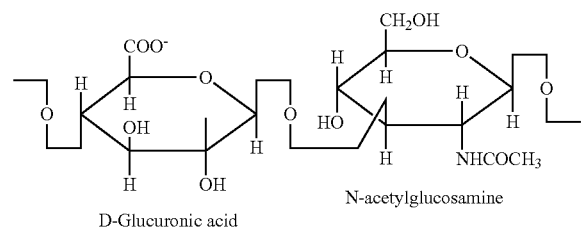

D-Glucuronic acid   N-acetylglucosamine wherein the extract of Aloe vera comprises 60 to 95% by weight of hydrolysed polysaccharides having a molecular weight in the range of 2 to 3 kDa and 0.1 to 20% by weight polyphenols.

A preferred aspect of the present invention relates to a method of providing enhanced immunity to the external surface of a human or animal body comprising the step of applying a composition of the invention.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

By an extract is meant a material extracted from a plant source including fractions and derivatives of the extracted material.

By "A Personal Care Composition" as used herein, is meant to include a composition for topical application to the external surface of a human or animal body, preferably the human body and includes the skin, the scalp, the hair and the oral cavity. Such a composition may be generally classified as leave-on or rinse off, and includes any product applied to a human body for also improving immunity, appearance, cleansing, odor control, moisturisation or general aesthetics. It is preferably a leave-on product. The composition for skin care of the present invention can be in the form of a liquid, lotion, cream, gel, or toner, and may be applied with an implement or via a face mask, pad or patch. Preferably the composition is in the form of a cream, lotion or gel. "Skin" as used herein is meant to include skin on the face and body (e.g. neck, chest, back, arms, underarms, hands, legs, and buttocks).

The composition of the invention is also of relevance to applications on hair and scalp. The products for such application on scalp or hair generally provide benefits of providing strength to the hair fibre and for anti-dandruff benefits. Hair care compositions are delivered in the form of hair oils, hair care gels and creams and also in the form of wash off products like shampoos and conditioners.

The composition of the invention is also of benefit to oral care. Many oral care products like toothpaste, toothpowder, mouthwashes are of the wash-off type and in addition to these types of products, the present invention can be formulated in the form of gels, creams and ointments of the leave-on type for tooth and gum care.

The present invention relates to an combination of an extract of Aloe vera and a hyaluronic acid polymer having a molecular weight of from 5 to 60 kDa.

Aloe vera also known as Aloe barbadensis Miller belongs to the Liliaceae family, which contains hundreds of species. Aloe is found only in cultivation and has no naturally occurring populations. It is a stemless or very short-stemmed succulent plant growing up to a height of about 60 to 100 cm. The leaves are thick and fleshy and appear in green to grey-green colour. Many of the health benefits associated with Aloe vera have been attributed to the polysaccharides contained in the gel of the leaves. A chemical analyses reveals that Aloe gel contains mannose polymers with some glucose and other sugars, among which the most important is Acemannan. Besides these, other components such as glycoproteins, enzymes, amino acids, vitamins, and minerals are known to occur. Extracts from Aloe vera are widely used in the cosmetics and alternative medicine industries, being marketed as having rejuvenating or soothing properties.

The leaf of Aloe vera is especially preferred for preparing the extract of the invention.

The Aloe vera extract useful for use in the present invention comprises (i) 60 to 95% by weight of hydrolysed polysaccharides having a molecular weight in the range of 2 to 3 kDa and 0.1 to 20% polyphenols. Preferably the polysaccharides are hydrolysed by trifluoroacetic acid (TFA). Such a fraction generally comprises less than 5% polyphenols, more preferably 0.1 to 2% polyphenols. Aqueous extract of Aloe vera generally available comprises 30 to 60% polysaccharides having molecular weight of less than 10 kD and 10 to 20% polyphenols. Further selective hydrolysis of this fraction is carried out to substantially remove most of the side chain monosaccharides to prepare an active which is even further efficacious. Thus the selective polysaccharides of the present invention preferably comprise the polymer backbone:

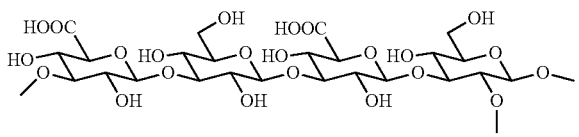

As a further preferred aspect, the polysaccharide fraction of the extract comprises higher than 30% polysaccharides having the above polymer backbone. They have found that this fraction is very effective in enhancing tight junction for the purposes of the present invention.

The composition of the invention preferably comprises 0.1 to 10% by weight extract of Aloe vera on dry weight basis, preferably 0.1 to 5% by weight.

The highly preferred extract of Aloe vera is obtainable using a process comprising the following steps:
 (i) extracting Aloe vera with water;
 (ii) passing the extract through a 10 KD cut-off filter to obtain a low molecular weight
 (iii) precipitating the polysaccharides in the low molecular weight fraction by addition of ethanol;
 (iv) hydrolysing the polysaccharides with trifluoroacetic acid;
 (v) removing the excess acid; and
 (vi) precipitating the hydrolyzed polysaccharides using ethanol; and
 (vii) drying the precipitate to yield the extract.

The trifluoroacetic acid is preferably removed from the mixture using the process of evaporation.

Hyaluronic acid was purchased from commercial sources like Sigma.

The composition of the invention comprises a hyaluronic acid polymer having a molecular weight from 5 to 60 kDa, the hyaluronic acid having the monomeric structure FIG. 1. Chemical structure of HA

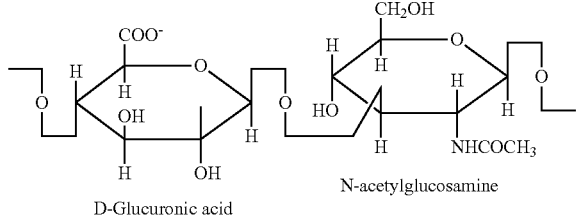

The hyaluronic acid polymer preferably has a molecular weight from 45 to 55 kDa. The composition preferably comprises 0.1 to 10% by weight hyaluronic acid polymer, more preferably 0.1 to 5% by dry weight of the composition.

Without wishing to be bound by theory, the present inventors believe that the benefits of the present invention occur through enhancing Inter-cellular Tight junctions (TJs).

Presence of TJs in epithelium enables it to act as barrier and stop the entry of pathogens and foreign substances into the human body. TJ is a multi protein complex made of transmembrane and cytoplasmic proteins. TJ barriers are disrupted by pathogens and pathogens have evolved different strategies to remove the TJs and gain entry into host tissue. The major effect of loss of TJs due to pathogen infection can be seen in diseases like diarrhoea in the intestines and periodontitis in the oral cavity. Health and hygiene of the oral, gut and skin tissues depends on the stability of the TJs. The present inventors have prepared the specific combination of the Aloe vera extract together with the hyaluronic acid polymer which combination interacts synergistically with the TJs thereby enhancing their stability and tightness to provide the benefits mentioned above.

According to a preferred aspect of the present invention there is provided a personal care composition additionally comprising a cosmetically acceptable base.

The cosmetically acceptable base is such as to provide a product for skin, oral, hair or scalp care.

The cosmetically acceptable base especially when prepared as a cream or lotion preferably comprises a fatty acid and optionally a soap of the fatty acid. When the fatty acid is present it is preferred to include it in 1 to 25%, preferably 3 to 20% by weight of the composition. When soap is is included it is preferably added at 0.1 to 10%, more preferably 0.1 to 3%. $C_{12}$ to $C_{20}$ fatty acids are especially preferred among the fatty acids for use in the composition of the present invention. Further more preferred fatty acids are $C_{14}$ to $C_{18}$ fatty acids. In creams, the fatty acid is preferably substantially a mixture of stearic acid and palmitic acid. Soaps in cream base include alkali metal salt of fatty acids, like sodium or potassium salts The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the composition is within the scope of the present invention. The cosmetically acceptable base is usually from 10 to 99.9%, preferably from 50 to 99% by weight of the composition. The cosmetically acceptable base preferably includes water. Water is preferably included in 35 to 90%, more preferably 50 to 85%, further more preferably 50 to 80% by weight of the composition.

When a skin or scalp care composition is prepared as a gel it primarily comprises high amount of water from 50 to 99% water which is thickened with one or more polymers. Polymers of natural or synthetic origin may be used. When of synthetic origin, it is preferably a polyacrylate polymer.

The skin or scalp care composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

When the composition is directed to oral care application, the cosmetically acceptable base is an orally acceptable base. The orally acceptable base is selected from water, calcium carbonate, silica or an orally acceptable surfactant. A preferred orally acceptable base is a mixture of water and surfactant. Preferred orally acceptable surfactant are an alkali metal alkyl sulphate or a betaine. The orally acceptable base depends on the format in which the oral care composition is delivered. The amount of orally acceptable base included in the composition of the invention also depends on the type if base included and is generally in the broad range of 0.05 to 99.9%, preferably 1 to 90%, further more preferably 5 to 70% by weight of the composition. Suitable formats of the composition as per the invention are an antiseptic mouthwash, a toothpaste or a toothpowder, preferably a toothpaste or a toothpowder.

Mouthwash

When the composition is formulated as an antiseptic mouthwash, the orally acceptable base is a mixture of water and surfactant. The antimicrobial mouthwash composition of the invention preferably comprises 0.05 to 10%, more preferably 0.05 to 8%, most preferably 0.5 to 5% of a surfactant by weight of the composition. The surfactant is preferably of the cationic, anionic, or zwitterionic class, most preferably of the cationic class. When anionic surfactant is present it is preferably chosen from alkali or alkaline earth metal salts of alkyl sulphonic acid, fatty acid, or alkyl ether sulphate. When zwitterionic surfactant is present it is preferably chosen from betaines, sulphobetaines, hydroxyl sulphobetaines, or amino carboxylates When a cationic surfactant is present it is benzalkonium chloride, alkyl pyridinium chloride or quaternary ammonium gemini surfactants.

Toothpaste

The composition of the invention may be delivered in a toothpaste format. When the composition is a toothpaste, the orally acceptable base is an abrasive which may be calcium carbonate or abrasive silica. When calcium carbonate is the abrasive, the toothpaste is in the opaque paste format. When abrasive silica is used, the toothpaste is usually delivered in the transparent gel format. Toothpastes also preferably comprise a surfactant in 2 to 15% by weight of the composition. Preferred surfactants are anionic or amphoteric in nature. Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10-018 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Opaque Toothpaste

When calcium carbonate is the abrasive, it is usually present in 15 to 70%, more preferably in 30 to 60% by weight of the composition.

In addition to calcium carbonate, one can also include abrasive silica in opaque toothpastes for enhanced abrasive action. The abrasive silica may be included in 4 to 15%, preferably 6 to 12%, and further more preferably 7 to 10%. Alternatively perlite may be included in 0.0.1 to 2%, preferably in 0.1 to 0.8%, further more preferably 0.3 to 0.7% by weight of the composition.

Water in these toothpastes is generally included in 15 to 40%, preferably 20 to 30% by weight of the composition.

Preferred compositions include a humectant, e.g. xylitol, glycerol or sorbitol. Glycerol and sorbitol are particularly preferred. Preferably, the compositions include 0.1 to 20 wt % humectant. More preferred compositions include 1 to 15 wt % humectants while further preferred compositions include 5 to 13 wt % humectants.

Gel Toothpaste

Preferred compositions to prepare gel toothpaste comprise an abrasive silica. They preferably have a low refractive index in the range of 1.41-1.47, preferably 1.435-1.445, more preferably having a weight mean particle size of between 5 and 15 micrometer, a BET (nitrogen) surface area of between 10 and 100 $m^2/g$ and an oil absorption of about 70-150 $cm^3/100$ g. The amount of these silicas in the composition generally ranges from 2-60% by weight, usually 2-20% by weight and more preferably 5 to 12 wt %.

Thickening silica may also be incorporated in gel toothpastes. They are usually incorporated in 4 to 12%, preferably 5 to 10% by weight of the composition. Water in these toothpastes is generally included in 8 to 14%, preferably 8 to 10% by weight of the composition. These amounts of water are exclusive of water which are incorporated in the composition from aqueous solutions of other ingredients e.g. sorbitol.

The compositions for any type of toothpaste (opaque or gel type) may also include an anti-caries agent, binders, thickeners, flavours, stabilizing agents, polymers, vitamins, buffers and anti-calculus agents.

According to yet another aspect of the present invention there is provided a method of providing enhanced immunity to an external surface of a human or animal body comprising the step of applying a composition of the invention. By enhanced immunity is meant immunity better than that provided by extract of Aloe vera alone or that provided by hyaluronic acid alone.

According to yet another aspect of the present invention there is provided a personal care composition comprising an extract of Aloe vera; and a hyaluronic acid polymer having a molecular weight from 5 to 60 kDa, the hyaluronic acid having the monomeric structure FIG. 1. Chemical structure of HA

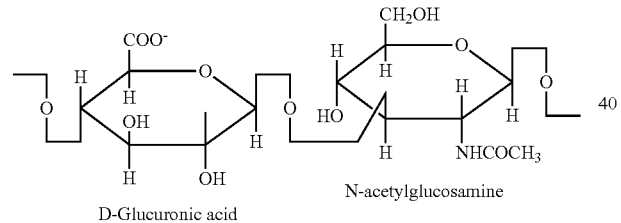

D-Glucuronic acid    N-acetylglucosamine for providing enhanced immunity to an external surface of a human or animal body.

According to yet another aspect of the present invention there is provided use of the personal care composition of the invention for imparting enhanced immunity to an external surface of a human or animal body.

The use is preferably non-therapeutic.

The invention will now be illustrated with the help of the following non-limiting example.

EXAMPLES

Examples A to C and 1

Efficacy of a Aloe Vera Fraction in Combination with a Hyaluronic Acid Polymer in Enhancing Inter-Cellular Tight Junctions Various samples were prepared as described below:
Preparation of Aloe fractions:
Spray dried Aloe vera leaf gel powder (aqueous extract) was obtained from commercial sources. This was then dissolved in water. A less than 10 KD fraction was then prepared by size exclusion and centrifugation. This fraction was then concentrated to reduce the volume (approx. from 5 ml to 1 ml) and 5 times volume of ethanol was added to the solution to precipitate out the polysaccharides. The solution was then and allowed to stay for 30 minutes for complete precipitation. The solution was centrifuged to collect the precipitate. The precipitate was repeatedly washed with ethanol (3 times) and then dried to obtain an aloe polysaccharide fraction (F1).

F1 fraction was hydrolysed under reflux condition using trifluoroacetic acid (TFA) (1 g of F1 in 2.5 ml 2M TFA) for 2 hours. After hydrolysis, the solution was concentrated to dryness. TFA was completely removed by repeatedly stripping off by adding toluene/methanol.

To the dried material, 1.5 ml water was added to dissolve the material completely. 5 times the volume of ethanol was added to precipitate out partially hydrolysed polysaccharides. Polysaccharides were separated from this solution by centrifugation, repeatedly washed with ethanol and then dried to get the most preferred fraction which was designated as Fraction F2.

Example—A

Control Sample signifies cells without any treatment.

Example—B

Cells were treated with 500 μg/ml concentration of Fraction F2 which was prepared as described hereinabove. The molecular weight of this fraction is around 2 KDa.

Example—C

Cells were treated with Hyaluronic acid (1 mg/ml) obtained from commercial sources.

Example 1

Cells treated with Hyaluronic acid (1 mg/ml) and 500 μg/ml concentration of Fraction F2 which is obtained as described hereinabove. The molecular weight of this fraction is around 2 KDa. The % of hydrolyzed polysaccharides in this fraction was measured to be ~91%. The polyphenol content in this fraction was ~2%.

The above samples were analysed for their ability to enhance inter-cellular tight junctions using the following procedure:
Measurement of TEER:

TEER stands for Trans Epithelial Electrical Resistance. This measures the stability of the tight junctions barrier. The procedure is as follows:

1. Millipore cell culture inserts (Millipore; cat no: PIHT12R48) were placed in a 24 well plate.

2. 500 μl of media were dispensed in the space within the well but outside the insert.

3. Keratinocytes (LONZA, cat no 192907) in KGM (LONZA, cat no: CC3111) were trypsinzes and resuspended. 80,000 cells/well (in 500 μl of media) were seeded into the inserts and incubated at 37° C. in 5% $CO_2$.

4. On day 1, the Trans Epithelial Electrical Resistance was measured (using Millicell ERS-2 Voltohmmeter from Millipore) in each of the wells.T 5. The used media from the wells were replaced with fresh KGM/actives (200 µl within the chamber and 800 µl outside the chamber) and incubated at 37° C. in 5% $CO_2$.

6. Steps 4-5 were repeated up to day 5.

7. The experiment was terminated by adding sodium hypochlorite (as a part of safe disposal of cells).

The data in the table shows the TEER values on Day 5, which correlates with the barrier stability at the end of day 5.

The data on the efficacy as measured using TEER value is summarised in Table—1.

TABLE 1

| Example | TEER values At day 5 | Standard deviation |
|---|---|---|
| A | 99 | 1.3 |
| B | 1197 | 12.6 |
| C | 107 | 2.9 |
| 1 | 1933 | 64.3 |

The data in Table—1 indicates that an Aloe vera extract in combination with a hyaluronic acid having the molecular weight as per the invention (Example—1) provides for synergistic tight junction enhancement indicative of improved immunity compared to the individual components.

Another set of experiments were performed to distinguish the benefit of the composition of the present invention with comparative controls as disclosed below:

Example D

Cells were treated with Hyaluronic acid (1 mg/ml) obtained from commercial sources.

Example E

Cells were treated with 500 µg/ml concentration of Aloe vera gel aqueous extract obtained after removing the less than 10 KD fraction as described in the previous section (greater than 10 KD fraction).

Example F

Cells were treated with 500 µg/ml concentration of Aloe vera gel aqueous extract obtained after removing the less than 10KD fraction as described in the previous section (greater than 10 KD fraction) and Hyaluronic acid (1 mg/mL).

Example 2

Cells treated with Hyaluronic acid (1 mg/ml) and 500 µg/ml concentration of Fraction F2 which is obtained as described hereinabove. The molecular weight of this fraction is around 2 KDa. The % of hydrolyzed polysaccharides in this fraction was measured to be ~91%. The polyphenol content in this fraction was ~2%.

The protocol of the experiments and the measurement of TEER value are same as mentioned above.

The results of these experiments are summarized below in Table 2:

TABLE 2

| Example | TEER values at Day 5 | S.D. |
|---|---|---|
| Control (only cells, no fraction) | 131 | 2.99 |
| D | 301 | 7.05 |
| E | 378 | 2.16 |
| F | 625 | 4.24 |
| 2 | 999 | 14.98 |

From the above table it is clear that the composition as per present invention (Example 2, which comprises TFA hydrolyzed polysaccharides and hyaluronic acid) provides much enhanced tight junction enhancement when compared with the Example D, E and F.

The invention claimed is:

1. A personal care composition comprising
   (i) an extract of Aloe vera; and
   (ii) a hyaluronic acid polymer having a molecular weight from 5 to 60 kDa, the hyaluronic acid having the monomeric structure;

FIG. 1. Chemical structure of HA

D-Glucuronic acid    N-acetylglucosamine wherein the extract of Aloe vera comprises 60 to 95% by weight of hydrolysed polysaccharides having a molecular weight in the range of 2 to 3 kDa and 0.1 to 20% by weight polyphenols.

2. A composition as claimed in claim 1 wherein the extract of Aloe vera comprises about 0.1 to 2% by weight polyphenols.

3. A composition as claimed in claim 1 comprising higher than 30% by weight of polysaccharide comprising the polymer backbone 4. A composition as claimed in claim 1 wherein the hyaluronic acid polymer has a molecular weight from 45 KDa to 55 kDa.

5. A composition as claimed in claim 1 comprising about 0.05 to 10% by weight extract of Aloe vera.

6. A composition as claimed in claim 1 comprising about 0.05 to 5% by weight extract of Aloe vera.

7. A composition as claimed in claim 1 comprising about 0.1 to 10% by weight hyaluronic acid polymer.

8. A composition as claimed in claim 1 comprising about 0.1 to 5% by weight hyaluronic acid polymer.

9. A composition of claim 1 further comprising a cosmetically acceptable base comprising a fatty acid, fatty acid salt, natural or synthetic polymer, water, calcium carbonate, silica, orally acceptable surfactant, or a combination of two or more thereof.

10. A composition as claimed in claim 9, wherein the composition comprises about 0.1 to 5% by weight of the hyaluronic acid polymer; about 0.05 to 5% by weight of the extract of Aloe vera; and about 50 to 99% by weight of the cosmetically acceptable base; wherein:
   the extract of Aloe vera comprises about 91 to 95% by weight of hydrolysed polysaccharides and about 0.1 to 5% by weight polyphenols; and
   the cosmetically acceptable base comprises water.

11. A composition as claimed in claim 10, wherein the composition comprises about 0.05 to 0.1% by weight of the extract of Aloe vera.

12. A composition as claimed in claim 10, wherein the the extract of Aloe vera comprises about 0.1 to 2% by weight polyphenols.

13. A composition as claimed in claim 10, wherein the composition comprises about 85 to 99% by weight of the cosmetically acceptable base.

14. A method of providing enhanced immunity to an external surface of a human or animal body comprising applying the composition of claim 1 to the external surface of the human or animal body, wherein the immunity of the external surface after applying the composition is greater than the immunity of the external surface after applying the extract of Aloe vera alone to the external surface or after applying the hyaluronic acid polymer alone to the external surface, wherein immunity is measured by trans epithelial electrical resistance (TEER).

15. The method of claim 14, wherein the immunity of the external surface after applying the composition is synergistic compared to immunity provided by the extract of Aloe vera alone and immunity provided by the hyaluronic acid polymer alone.

16. A method of providing enhanced immunity to an external surface of a human or animal body comprising applying the composition of claim 10 to the external surface of the human or animal body, wherein the immunity of the external surface after applying the composition is greater than the immunity of the external surface after the extract of Aloe vera is applied alone to the external surface or after the hyaluronic acid polymer is applied alone to the external surface, wherein immunity is measured by trans epithelial electrical resistance.

17. The method of claim 16, wherein the immunity of the external surface after applying the composition is synergistic compared to immunity provided by the extract of Aloe vera alone and immunity provided by the hyaluronic acid polymer alone.

* * * * *